United States Patent [19]
Fujishima et al.

[11] Patent Number: 5,637,736
[45] Date of Patent: Jun. 10, 1997

[54] PROCESS FOR PREPARING 1-BROMOALKYLBENZENE DERIVATIVES AND INTERMEDIATES THEREOF

[75] Inventors: Hiroaki Fujishima, Misawa; Yasunobu Miyamoto, Osaka; Masayoshi Minai, Shiga; Tsutomu Matsumoto, Kyoto; Hideki Ushio, Osaka; Takayuki Higashii, Kanagawa, all of Japan

[73] Assignee: Sumitomo Chemical Company, Limited, Osaka, Japan

[21] Appl. No.: 286,411

[22] Filed: Aug. 5, 1994

[30] Foreign Application Priority Data

| Aug. 6, 1993 | [JP] | Japan | 5-196039 |
| Jan. 12, 1994 | [JP] | Japan | 6-001711 |
| Jan. 14, 1994 | [JP] | Japan | 6-002492 |

[51] Int. Cl.$^6$ .................................................. C07D 319/14
[52] U.S. Cl. .................................................. 549/362; 585/24
[58] Field of Search .................................................. 549/362; 585/24

[56] References Cited

U.S. PATENT DOCUMENTS

| 4,228,106 | 10/1980 | Martan | 570/197 |
| 4,292,459 | 9/1981 | Cardenas et al. | 585/641 |
| 5,181,992 | 1/1993 | Commandeur et al. | 203/29 |

FOREIGN PATENT DOCUMENTS 0403331  12/1990  European Pat. Off. .

OTHER PUBLICATIONS

Kharasch et al, J. Organic Chemistry, vol. 2, pp. 195–197 (1937).

Chemical Abstracts, 11242g (1963).

Oae et al, J. Am. Chem. Soc., vol. 75, pp. 5037–5039 (1953).

Org. Synth. Coll., vol. 4, pp. 748–752.

Friedman et al, J. Am. Chem. Soc., vol. 96, No. 22, pp. 7101–7103 (1974).

Patent Abst. of Japan, vol. 7, No. 205 (C185) (Sep. 9, 1983).

*Primary Examiner*—Amelia Owens
*Attorney, Agent, or Firm*—Birch, Stewart, Kolasch & Birch, LLP

[57] ABSTRACT

A 1-bromoalkylbenzene derivative is prepared by reacting a phenylalkene derivative with hydrogen bromide in the presence of a non-polar solvent. The phenylalkene derivative is prepared by reacting an alkenyl halide with metal magnesium to form a Grignard reagent, and then reacting the Grignard reagent with a benzyl halide derivative. An allyl Grignard reagent is prepared by reacting continuously an allyl halide derivative with metal magnesium in an organic solvent, in which the allyl halide derivative and metal magnesium are continuously added to the reaction system and the allyl Grignard reagent formed is continuously removed from the reaction system. The processes provide the intended compounds in high yields, high selectivities and high purities.

8 Claims, No Drawings

PROCESS FOR PREPARING 1-BROMOALKYLBENZENE DERIVATIVES AND INTERMEDIATES THEREOF

BACKGROUND OF THE INVENTION

1. Field of the Invention

The present invention relates to a process for preparing a 1-bromoalkylbenzene derivative. The invention also relates to a process for preparing an allyl Grignard reagent which can be an intermediate of the 1-bromoalkylbenzene derivative.

2. Description of the Related Art

1-Bromoalkylbenzene derivatives are useful substances as intermediates for medicines, agrochemicals, etc. For example, they can be important intermediates of the compound of the formula:

(VIII)

[Structure: phenyl—(CH2)3—O—(CH2)6—NH—CH2—CH(OH)—phenyl(OH)(OH)]

which is useful as a medicine.

A 1-bromoalkylbenzene derivative of the general formula:

(IX)

[Structure: R-substituted phenyl—(CH2)n—CH2—CH2—Br]

wherein R represents a hydrogen atom, a lower alkyl group or a lower alkoxy group, and n is an integer of 1 to 8, may be prepared by reacting a phenylalkene derivative of the general formula:

(X)

[Structure: R-substituted phenyl—(CH2)n—CH=CH2]

wherein R and n are the same as defined above, with hydrogen bromide. However, when the reaction of the phenylalkene derivatives of the general formula (X) with hydrogen bromide is carried out by conventional methods, for examples, using (1) an aqueous hydrobromic acid solution, or (2) a hydrobromic acid solution in acetic acid or propionic acid, there are problems that the reaction does not proceeds, or the selectivity of the 1-bromoalkylbenzene of the general formula (IX) is low and the isomer the general formula:

(XI)

[Structure: R-substituted phenyl—(CH2)n—CH(Br)—CH3]

wherein R and n are the same as defined above, is by-produced.

On the other hand, it is known to prepare the phenylalkene of the general formula (X) in which R is H and n is 2 in the following two ways: One process comprise the step of reacting phenetyl magnesium bromide with vinyl chloride in the presence of nickel acetylacetonate to obtain 4-phenyl-1-butene. The other process comprises the steps of reacting toluene with 1,3-butadiene in the presence of sodium to form 5-phenyl-2-pentene and then reacting it with ethylene in the presence of tetrabutyl tin and rhenium oxide to obtain 4-phenyl-1-butene.

However, both of the above processes are not satisfactory since they use sodium which is difficult to handle industrially, or use expensive catalysts.

It is known to prepare an allyl Grignard reagent in the following two ways: One process comprises the step of adding one mole of allyl chloride to 2.4 moles of magnesium in tetrahydrofuran which is cooled to $-15°$ C. over a period of 12 hours to obtain allyl magnesium chloride. The other process comprises the step of adding dropwise one mole of allyl bromide to 2.4 mole of magnesium in tetrahydrofuran which is cooled to $0°$ C. over a period of 17 hours to obtain allyl magnesium bromide.

However, the processes use a large amount of the solvent, require the long periods of reaction time at the low temperatures and, in addition, are difficult to obtain the products in high yields since Wurtz-type reactions proceed rapidly (see Org. Syn., Coll. Vol. IV, p 749).

SUMMARY OF THE INVENTION

It is an object of the present invention to provide an industrially advantageous novel process for preparing a 1-bromoalkylbenzene derivative.

It is another object of the present invention to provide a process for preparing an allyl Grignard reagent which can be an intermediate of the 1-bromoalkylbenzene derivative.

The present invention provides a process for preparing a 1-bromoalkylbenzene derivative of the general formula:

(I)

[Structure: phenyl with R¹, R², R³ substituents—(CH2)n+2—Br]

wherein $R^1$, $R^2$ and $R^3$ independently represent a hydrogen atom, a halogen atom, a lower alkyl group containing 1 to 5 carbon atoms or a lower alkoxy group containing 1 to 5 carbon atoms, or $R^1$ and $R^2$ together form a methylenedioxy group or an ethylenedioxy group when $R^3$ is a hydrogen atom, and n is an integer of 1 to 8, comprising the step of reacting a phenylalkene derivative of the general formula:

(II)

[Structure: phenyl with R¹, R², R³ substituents—(CH2)n—CH=CH2]

wherein $R^1$, $R^2$, $R^3$ and n are the same as defined above, with hydrogen bromide in the presence of a non-polar solvent to form the 1-bromoalkylbenzene derivative of the general formula (I).

The phenylalkene derivative of the general formula (II) can be prepared by a process comprising the steps of reacting an alkenyl halide of the general formula:

$$CH_2=CH-(CH_2)_{n-1}-X \quad \text{(III)}$$

wherein X represents a chlorine atom or a bromine atom, and n is the same as defined above, with metal magnesium to form a Grignard reagent of the general formula:

$$CH_2=CH-(CH_2)_{n-1}-MgX \quad \text{(IV)}$$

wherein X and n are the same as defined above; and then reacting the Grignard reagent of the general formula (IV) with a benzyl halide derivative of the general formula:

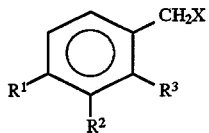

(V)

wherein $R^1$, $R^2$, $R^3$ and X are the same as defined above, to form the phenylalkene derivative of the general formula (II).

The present invention also provides a process for preparing an allyl Grignard reagent of the general formula:

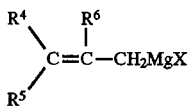

(VI)

wherein $R^4$, $R^5$ and $R^6$ independently represent a hydrogen atom or an alkyl group containing 1 to 4 carbon atoms and X is the same as defined above, comprising the step of reacting an allyl halide derivative of the general formula:

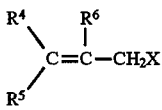

(VII)

wherein $R^4$, $R^5$, $R^6$ and X are the same as defined above, with metal magnesium in an organic solvent to form the allyl Grignard reagent of the general formula (VI), wherein the allyl halide derivative of the general formula (VII) and metal magnesium are continuously added to the reaction system and the allyl Grignard reagent of the general formula (VI) formed is continuously removed from the reaction system.

DETAILED DESCRIPTION OF THE INVENTION

According to the present invention, a 1-bromoalkylbenzene derivative of the general formula (I) is prepared from hydrogen bromide and a phenylalken derivative of the general formula (II), which can be derived from a benzyl halide derivative of the general formula (V) and a Grignard reagent of the general formula (IV).

At first, the process for preparing the phenylalkene derivative of the general formula (II) according to the present invention will be illustrated.

For this purpose, the alkenyl halide of the general formula (III) is reacted with metal magnesium to form the Grignard reagent of the general formula (IV).

Specific examples of the alkenyl halide used are vinyl chloride, ally chloride, 4-chloro-1-butene, 5-chloro-1-pentene, 6-chloro-1-hexene, 7-chloro-1-heptene, 8-chloro-1-octene, 9-chloro-1-nonene, vinyl bromide, allyl bromide, 4-bromo-1-butene, 5-bromo-1-pentene, 6-bromo-1-hexene, 7-bromo-1-heptene, 8-bromo-1-octene, 9-bromo-1-nonene, etc.

The alkenyl halide is usually used in an amount of 0.5 to 1.5 moles, preferably 1 to 1.3 moles per mole of metal magnesium. When the amount of the alkenyl halide exceeds 1.5 moles, a Wurtz-type reaction tends to occur, which lowers the yield of the Grignard reagent.

The reaction may be carried out in the presence of a solvent. Preferred examples of the solvent are tetrahydrofuran, or a mixed solvent thereof with tert.-butyl methyl ether or an aromatic hydrocarbon such as benzene, toluene, xylene, etc. From the view point of solvent recovery, the mixed solvent of tetrahydrofuran with tert.-butyl methyl ether or an aromatic hydrocarbon is more preferred than tetrahydrofuran alone. When the mixed solvent is used, the mixing ratio is determined depending on the kind of the solvent used. For example, in the case of the tetrahydrofuran—tert.-butyl methyl ether mixed solvent, a volume ratio of tert.-butyl methyl ether to tetrahydrofurane is from 0.1 to 3, preferably from 0.5 to 1.5. In the case of the tetrahydrofuran—toluene mixed solvent, a volume ratio of toluene to tetrahydrofuran is from 0.1 to 9, preferably from 0.4 to 5.5. A higher mixing ratio is preferred in order to reduce the amount of tetrahydrofuran used. However, when the mixing ratio exceeds the above limit, the desired Grignard reagent cannot be prepared efficiently. From the view point of stirring of a reaction mass in the next step, a too low mixing ratio is not preferred.

The solvent is used in an amount of 5 to 30 times, preferably 8 to 20 times the alkenyl halide by weight. When the solvent is less than the above amount, the Wurtz-type reaction is apt to occur, decreasing the yield of the Grignard reagent. On the other hand, the excessive use of the solvent is uneconomical although the yield is not affected.

The reaction may be carried out at a temperature of −50° to 50° C., preferably −10° to 20° C. When the reaction temperature exceeds 50° C., the Wurtz-type reaction tends to occur and the yield of the Grignard reagent is decreased.

The reaction may be carried out by adding dropwise the alkenyl halide to a mixture of metal magnesium and the solvent with stirring.

Then the phenylalkene derivative of the general formula (II) is prepared by reacting the Grignard reagent of the general formula (IV) obtained above with a benzyl halide derivative of the general formula (V).

$R^1$, $R^2$ and $R^3$ in the benzyl halide derivative of the general formula (V) include a hydrogen atom, a fluorine atom, a chlorine atom, a bromine atom, an iodine atom, a methyl group, an ethyl group, a propyl group, a butyl group, a methoxy group, an ethoxy group, a propoxy group, a butoxy group, etc.

Specific examples of the benzyl halide derivative are benzyl chloride, fluorobenzyl chloride, chlorobenzyl chloride, bromobenzyl chloride, iodobenzyl chloride, methylbenzyl chloride, ethylbenzyl chloride, propylbenzyl chloride, butylbenzyl chloride, methoxybenzyl chloride, ethoxybenzyl chloride, propoxybenzyl chloride, butoxybenzyl chloride, benzyl bromide, fluorobenzyl bromide, chlorobenzyl bromide, bromobenzyl bromide, iodobenzyl bromide, methylbenzyl bromide, ethylbenzyl bromide, propylbenzyl bromide, butylbenzyl bromide, methoxybenzyl bromide, ethoxybenzyl bromide, propoxybenzyl bromide, and butoxybenzyl bromide, wherein the subsituents in the benzyl group may be positioned at any of $R^1$, $R^2$ and $R^3$; and 3,4-methylenedioxybenzyl chloride, 3,4-methylenedioxybenzyl bromide, 3,4-ethylenedioxybenzyl chloride, 3,4-ethylenedioxybenzyl bromide, etc.

The benzyl halide derivative is used in amount of 0.2 to 1.2 moles, preferably 0.4 to 1 mole per mole of the Grignard reagent.

The reaction is carried out optionally in the presence of a catalyst. Although the reaction proceeds without the catalyst, the use of the catalyst accelerates the reaction to give a higher yield of the phenylalkene derivative of the general formula (II) in some cases. Examples of the catalyst are nickel catalysts such as divalent nickel complexes, for example, bis(triphenylphosphine) nickel chloride, bis(1,3- diphenylphosphinopropane) nickel chloride, nickel acetylactonate, etc. The catalyst is usually used in an amount of 0.001 to 10 mole %, preferably 0.1 to 3 mole %, based on the benzyl halide derivative.

The reaction temperature is usually in a range of 0° to 80° C., preferably 10° to 70° C.

Although the manner for the addition of the reactants is not particularly restricted, the benzyl halide derivative is usually added dropwise to the Grignard reagent solution during an appropriate period of time.

The isolation of the phenylalkene derivative produced from the reaction mixture can be usually carried out in the following manner: After the completion of the reaction, the reaction mixture is posttreated with water, an aqueous acidic solution, or an aqueous ammonium chloride solution which are conventionally used for the decomposition of Grignard reagents to decompose the Grignard reagent, followed by the extraction of the phenylalkene derivative with an organic solvent. Then the desired phenylalkene derivative can be isolated by conventional isolating techniques, for example, washing, concentration and distillation.

Examples of the phenyl alkene derivative are 3-phenyl-1-propene, 4-phenyl-1-butene, 5-phenyl-1-pentene, 6-phenyl-1-hexene, 7-phenyl-1-heptene, 8-phenyl1-octene, 9-phenyl-1-nonene, 10-phenyl-1-decene, 3-(fluorophenyl)-1-propene, 3-(chlorophenyl)-1-propene, 3-(bromophenyl)-1-propene, 3-(iodophenyl)-1-propene, 4-(fluorophenyl)-1-butene, 4-(chlorophenyl)-1 -butene, 4-(bromophenyl)-1-butene, 4-(iodophenyl)-1-butene, 5-(fluorophenyl)-1-pentene, 5-(chlorophenyl)-1-pentene, 5-(bromophenyl)-1-pentene, 5-(iodophenyl)-1-pentene, 6-(fluorophenyl)-1-hexene, 6-(chlorophenyl)-1-hexene, 6-(bromophenyl)-1-hexene, 6-(iodophenyl)-1-hexene, 7-(fluorophenyl)-1-heptene, 7-(chlorophenyl)-1-heptene, 7-(bromophenyl)-1-heptene, 7-(iodophenyl)-1-heptene, 8-(fluorophenyl)-1-octene, 8-(chlorophenyl)-1-octene, 8-(bromophenyl)-1-octene, 8-(iodophenyl)-1-octene, 9-(fluorophenyl)-1-nonene, 9-(chlorophenyl)-1-nonene, 9-(bromophenyl)-1-nonene, 9-(iodophenyl)-1-nonene, 10-(fluorophenyl)-1-decene, 10-(chlorophenyl)-1-decene, 10-(bromophenyl)-1-decene, and 10-(iodophenyl)-1-decene, wherein the substituents in the phenyl group may be positioned at any of $R^1$, $R^2$ and $R^3$; and 3-(methylphenyl)-1-propene, 3-(ethylphenyl)-1-propene, 3-(propylphenyl)-1-propene, 3-(butylphenyl)-1-propene, 4-(methylphenyl)-1-butene, 4-(ethylphenyl)-1-butene, 4-(propylphenyl)-1-butene, 4-(butylphenyl)-1-butene, 5-(methylphenyl)-1-pentene, 5-(ethylphenyl)-1-pentene, 5-(propylphenyl)-1-pentene, 5-(butylphenyl)-1-pentene, 6-(methylphenyl)-1-hexene, 6-(ethylphenyl)1-hexene, 6-(propylphenyl)-1-hexene, 6-(butylphenyl)-1-hexene, 7-(methylphenyl)1-heptene, 7-(ethylphenyl)-1-heptene, 7-(propylphenyl)-1-heptene, 7-(butylphenyl)-1-heptene, 8-(methylphenyl)-1-octene, 8-(ethylphenyl)-1-octene, 8-(propylphenyl)1-octene, 8-(butylphenyl)-1-octene, 9-(methylphenyl)-1-nonene, 9-(ethylphenyl)-1-nonene, 9-(propylphenyl)-1-nonene, 9-(butylphenyl)-1-nonene, 0-(methylphenyl)-1-decene, 10-(ethylphenyl)-1-decene, 10-(propylphenyl)-1-decene, 10-(butylphenyl)-1-decene, 3-(methoxyphenyl)-1-propene, 3-(ethoxyphenyl)-1-propene, 3-(propoxyphenyl)-1-propene, 3-(butoxyphenyl)-1-propene, 4-(methoxyphenyl)-1-butene, 4-(ethoxyphenyl)-1-butene, 4-(propoxyphenyl)-1-butene, 4-(butoxyphenyl)-1-butene, 5-(methoxyphenyl)-1-pentene, 5-(ethoxyphenyl)-1-pentene, 5-(propoxyphenyl)-1-pentene, 5-(butoxyphenyl)-1-pentene, 6-(methoxyphenyl)-1-hexene, 6-(ethoxyphenyl)-1-hexene, 6-(propoxyphenyl)-1-hexene, 6-(butoxyphenyl)-1-hexene, 7-(methoxyphenyl)-1-heptene, 7-(ethoyphenyl)-1-heptene, 7-(propoxyphenyl)-1-heptene, 7-(butoxyphenyl)-1-heptene, 8-(methoxyphenyl)-1-octene, 8-(ethoxyphenyl)-1-octene, 8-(propoxyphenyl)-1-octene, 8-(butoxyphenyl)-1-octene, 9-(methoxyphenyl)-1-nonene, 9-(ethoxyphenyl)-1-nonene, 9-(propoxyphenyl)-1-nonene, 9-(butoxyphenyl)1-nonene, 10-(methoxyphenyl)-1-decene, 10-(ethoxyphenyl)-1-decene, 10-(propoxyphenyl)-1-decene, 10-(butoxyphenyl)1-decene, 3-(3,4-methylenedioxy-phenyl)-1-propene, 3-(3,4-ethylenedioxy-phenyl)-1-propene, 4-(3,4-methylenedioxy-phenyl)-1-butene, 4-(3,4-ethylenedioxy-phenyl)-1-butene, 5-(3,4-methylenedioxy-phenyl)-1-pentene, 5-(3,4-ethylenedioxy-phenyl)-1-pentene, 6-(3,4-methylenedioxy-phenyl)-1-hexene, 6-(3,4-ethylenedioxy-phenyl)-1-hexene, 7-(3,4-methylenedioxy-phenyl)-1-heptene, 7-(3,4-ethylenedioxy-phenyl)-1-heptene, 8-(3,4-methylenedioxy-phenyl)-1-octene, 8-(3,4-ethylenedioxy-phenyl)1-octene, 9-(3,4-methylenedioxy-phenyl)-1-nonene, 9-(3,4-ethylenedioxy-phenyl)-1-nonene, 10-(3,4-methylenedioxy-phenyl)-1-decene, 10-(3,4-ethylenedioxy-phenyl)-1-decene, etc.

Then the 1-bromoalkylbenzene derivative of the general formula (I) is prepared by reacting the phenylalkene derivative of the general formula (II) with hydrogen bromide.

Hydrogen bromide is usually used in the form of gas, but can be used in the form of a hydrogen bromide solution in acetic acid or propionic acid which is readily commercially available. Hydrogen bromide may be used in an amount of at least the same mole as that of the phenylalkene derivative, usually in an amount of 1 to 10 moles per mole of it.

The reaction is usually carried out in the presence of a non-polar solvent which is inert to the reaction. Examples of the solvent are aliphatic hydrocarbons such as pentane, hexane, cyclohexane, etc; aromatic hydrocarbons such as benzene, toluene, etc.; or the mixture thereof. The amount of the solvent to be used is not particularly restricted.

The reaction can be carried out in the presence of a radical initiator. Examples of the radical initiator are peroxides such as benzoyl peroxide, tert.-butyl hydroperoxide, etc., AIBN, light, oxygen, etc. The amount of the radical initiator to be used is not particularly limited.

The reaction temperature may be usually in the range of −50° to 50° C., preferably at near a room temperature.

The reaction time depends on the reaction temperature, but is usually 5 minutes to one hour. Even when reaction time is too long, adverse effects would not be observed.

After the completion of the reaction, the desired 1-bromoalkylbenzene derivative can be isolated from the reaction mixture by conventional isolating techniques, for example, extraction, phase separation and distillation. If desired, it may be further purified by distillation and column chromatography.

Examples of the 1-bromoalkylbenzene derivative of the general formula (I) are 3-phenyl-1-bromopropane, 4-phenyl-1-bromobutane, 5-phenyl-1-bromopentane, 6-phenyl-1-bropmohexane, 7-phenyl-1-bromoheptane, 8-phenyl-1-bromooctane, 9-phenyl-1-bromononane, 10-phenyl-1-bromodecane, 3-(fluorophenyl)-1-bromopropane, 3-(chlorophenyl)-1-bromopropane, 3-(bromophenyl)-1-bromopropane, 3-(iodophenyl)-1-bromopropane, 4-(fluorophenyl)-1-bromobutane, 4-(chlorophenyl)-1-bromobutane, 4-(bromophenyl)-1-bromobutane, 4-(iodophenyl)-1-bromobutane, 5-(fluorophenyl)-1-bromopentane, 5-(chlorophenyl)-1-bromopentane, 5-(bromophenyl)-1-bromopentane, 5-(iodophenyl)-1-bromopentane, 6-(fluorophenyl)-1-bromohexane, 6-(chlorophenyl)-1-bromohexane, 6-(bromophenyl)-1-bromohexane, 6-(iodophenyl)-1-bromohexane, 7-(fluorophenyl)-1-bromoheptane, 7-(chlorophenyl)-1-bromoheptane, 7-(bromophenyl)-1-bromoheptane, 7-(iodophenyl)-1-bromoheptane, 8-(fluorophenyl)-1-bromooctane, 8-(chlorophenyl)-1-bromooctane, 8-(bromophenyl)-1-bromooctane, 8-(iodophenyl)-1-bromooctane, 9-(fluorophenyl)-1-bromononane, 9-(chlorophenyl)-1-bromononane, 9-(bromophenyl)-1-bromononane, 9-(iodophenyl)-1-bromononane, 10-(fluorophenyl)-1-bromodecane, 10-(chlorophenyl)-1-bromodecane, 10-(bromophenyl)-1-bromodecane, 10-(iodophenyt)-1-bromodecane, 3-(methylphenyl)-1-bromopropane, 3-(ethylphenyl)-1-bromopropane, 3-(propylphenyl)-1-bromopropane, 3-(butylphenyl)-1-bromopropane, 4-(methylphenyl)-1-bromobutane, 4-(ethylphenyl)-1-bromobutane, 4-(propylphenyl)-1-bromobutane, 4-(butylphenyl)-1-bromobutane, 5-(methylphenyl)-1-bromopentane, 5-(ethylphenyl)-1-bromopentane, 5-(propylphenyl)-1-bromopentane, 5-(butylphenyl)-1-bromopentane, 6-(methylphenyl)-1-bromohexane, 6-(ethylphenyl)-1-bromohexane, 6-(propylphenyl)-1-bromohexane, 6-(butylphenyl)-1-bromohexane, 7-(methylphenyl)-1-bromoheptane, 7-(ethylphenyl)-1-bromoheptane, 7-(propylphenyl)-1-bromoheptane, 7-(butylphenyl)-1-bromoheptane, 8-(methylphenyl)-1-bromooctane, 8-(ethylphenyl)-1-bromooctane, 8-(propylphenyl)-1-bromooctane, 8-(butylphenyl)-1-bromooctane, 9-(methylphenyl)-1-bromononane, 9-(ethylphenyl)-1-bromononane, 9-(propylphenyl)-1-bromononane, 9-(butylphenyl)-1-bromononane, 10-(methylphenyl)-1-bromodecane, 10-(ethylphenyl)-1-bromodecane, 10-(propylphenyl)-1-bromodecane, 10-(butylphenyl)-1-bromodecane, 3-(methoxyphenyl)-1-bromopropane, 3-(ethoxyphenyl)-1-bromopropane, 3-(propoxyphenyl)-1-bromopropane, 3-(butoxyphenyl)-1-bromopropane, 4-(methoxyphenyl)-1-bromobutane, 4-(ethoxyphenyl)-1-bromobutane, 4-(propoxyphenyl)-1-bromobutane, 4-(butoxyphenyl)-1-bromobutane,5-(methoxyphenyl)-1-bromopentane, 5-(ethoxyphenyl)1-bromopentane, 5-(propoxyphenyl)-1-bromopentane, 5-(butoxlphenyl)-1-bromopentane, 6-(methoxyphenyl)-1-bromohexane, 6-(ethoxyphenyl)-1-bromohexane, 6-(propoxyphenyl)-1-bromohexane, 6-(butoxyphenyl)-1-bromohexane, 7-(methoxyphenyl)-1-bromoheptane, 7-(ethoxylphenyl)-1-bromoheptane,7-(propoxyphenyl)-1-bromoheptane, 7-(butoxyphenyl)-1-bromoheptane, 8-(methoxyphenyl)1-bromooctane, 8-(ethoxyphenyl)-1-bromooctane, 8-(propoxyphenyl)-1-bromooctane, 8-(butoxyphenyl)-1-bromooctane, 9-(methoxyphenyl)-1-bromononane, 9-(ethoxyphenyl)-1-bromononane, 9-(propoxyphenyl)-1-bromononane, 9-(butoxyphenyl)-1-bromononane, 10-(methoxyphenyl)-1-bromodecane, 10-(ethoxyphenyl)-1-bromodecane, bromodecane, 10-(propoxyphenyl)-1-bromodecane, and 10-(butoxyphenyl)-1-bromodecane, wherein the substituents in the phenyl group may be positioned at any of $R^1$, $R^2$ and $R^3$; and 3-(3,4-methylenedioxyphenyl)-1-bromopropane, 3-(3,4-ethylenedioxy-phenyl)-1-bromopropane, 4-(3,4-methylenedioxy-phenyl)-1-bromobutane, 4-(3,4-ethylenedioxy-phenyl)-1-bromobutane, 5-(3,4-methylenedioxy-phenyl)-1-bromopentane, 5-(3,4-ethylenedioxy-phenyl)-1-bromopentane, 6-(3,4-methylenedioxy-phenyl)-1-bromohexane, 6-(3,4-ethylenedioxy-phenyl)-1-bromohexane, 7-(3,4-methylenedioxy-phenyl)-1-bromoheptane, 7-(3,4-ethylenedioxy-phenyl)-1-bromoheptane, 8-(3,4-methylenedioxy-phenyl)-1-bromooctane, 8-(3,4-ethylenedioxy-phenyl)-1-bromooctane, 9-(3,4-methylenedioxy-phenyl)-1-bromononane, 9-(3,4-ethylenedioxy-phenyl)-1-bromononane, 10-(3,4-methylenedioxy-phenyl)-1-bromodecane, 10-(3,4-ethylenedioxy-phenyl)-1-bromodecane, etc.

The present invention also relates to a process for preparing an allyl Grignard reagent of the general formula:

wherein $R^4$, $R^5$ and $R^6$ independently represent a hydrogen atom or an alkyl group containing 1 to 4 carbon atoms and X is the same as defined above, which can be used as a starting substance for preparing the above phenylalkene derivative, comprising the step of reacting continuously an allyl halide derivative of the general formula:

wherein $R^4$, $R^5$ and $R^6$ and X are the same as defined above, with metal magnesium in an organic solvent to form the allyl Grignard reagent of the general formula (VI). The process is characterized in that the allyl halide derivative of the general formula (VII) and metal magnesium are continuously added to the reaction system and the allyl Grignard reagent of the general formula (V) is continuously removed from the reaction system. The allyl Grignard reagent is very suitable for use as the Grignard reagent of the general formula (V) used in the above process.

The substituents $R^4$, $R^5$ and $R^6$ in the compounds of the general formulas (VI) and (VII) include a hydrogen atom, a methyl group, a ethyl group, a n-propyl group, an isopropyl group, a n-butyl group, an isobutyl group, a tert.-butyl group, etc.

The reaction may be, for example, carried out as follows: Into a reaction vessel having a branch, metal magnesium in an amount of 0 to 6 times the allyl halide derivative in mole to be added during an initial 1 hour, iodine in a small amount and a solvent are charged. The amount of the solvent to be charged is determined in such a manner that the reaction mixture begin to flow out of the reaction vessel through the branch, for example, 1 hour after the start of the addition of the allyl halide derivative. Then the allyl halide derivative dissolved in the solvent was continuously added through a pump. After heat is violently generated to confirm the initiation of the reaction, the reaction mixture is cooled to a preset temperature. At the same time with the initiation of the addition of the allyl halide derivative, metal magnesium is also begun to be continuously added through a rotary solid introducing apparatus in an equimolar amount to or more than that of the allyl halide derivative to be added. However, a large excessive amount of metal magnesium are not preferred since it is accumulated in the reaction system. The Grignard reagent which is formed and contained in the reaction mixture flowing out the reaction vessel through the branch is quantitatively determined every unit time. The time when the content of the Grignard reagent reaches a constant value is regarded as the time when the reaction system reaches a stationary state.

The above is the case wherein the residence time of the allyl halide derivative is 1 hour. The residence time can be controlled freely by varying the amount of the allyl halide derivative added through the pump.

Examples of the solvent used are tetrahydrofuran, or the mixed solvent thereof with tert.-butyl methyl ether or aromatic hydrocarbons such as benzene, toluene, xylene, etc. From the point of the view of solvent recovery, the mixed solvent of tetrahydrofuran with tert.-butyl methyl ether or an aromatic hydrocarbon is more preferred than a single solvent of tetrahydrofuran. When the mixed solvent is used, the mixing ratio is determined depending on the kind of the solvent used. For example, in the case of the tetrahydrofuran—tert.-butyl methyl ether mixed solvent, a volume ratio of tert.-butyl methyl ether to tetrahydrofuran is from 0.05 to 3.0, preferably from 0.5 to 1.5. In the case of the tetrahydrofuran/toluene mixed solvent, a volume ratio of toluene to tetrahydrofuran is from 0.05 to 9, preferably from 0.4 to 5.5.

The amount of the solvent used for dissolving the allyl halide derivative which is continuously added is such that the concentration of the allyl halide derivative is in the range of 0.02 to 0.5, preferably 0.05 to 0.2 mol/L. On the other hand, the amount of the solvent initially charged in the reaction vessel is not particularly restricted depending on the volume of the reaction vessel. However, it is preferred to use the solvent in an amount of approximately half the volume at which the reaction mixture begin to flow out of the reaction vessel through the branch. When the amount is too small, the Wurtz type reaction tends to occur to decrease the yield of the Grignard reagent. On the other hand, the use of the solvent in a too large amount is uneconomical although it does not affect the yield.

The amount of the metal magnesium initially charged in the reaction vessel is in the range of 0 to 6 moles, preferably 1 to 3 moles per mole of the allyl halide derivative. Metal magnesium has not always to be initially charged in the reaction vessel. On the other hand, the amount of the metal magnesium continuously added to the reaction vessel is usually in the range of not less than 1 mole, preferably 1 to 1.2 moles per mole of the allyl halide derivative. When it is less than 1 mole, the metal magnesium initially charged is consumed to lack magnesium in the reaction system and hence the Wurtz type reaction tends to occur to lower the yield of the Grignard reagent. When it exceeds 1.2 moles, an unconsumed amount of magnesium is accumulated in the reaction system although the yield is not affected. Magnesium can be added continuously or portionwise.

The amount of the allyl halide derivative added per unit time is not particularly restricted provided it is in a range which can control the reaction temperature and the residence time of the allyl halide. The amount which is suitable for a predetermined residence time should be selected.

The reaction is usually carried out at a temperature of −50° to 80° C., preferably −10° to 60° C. The reaction time, which is the residence time to the flowing out of the reaction mixture through the branch of the reaction vessel, is usually in the range of 0.1 to 5 hours, preferably 0.5 to 3 hours.

The quantitative determination of the Grignard reagent in the reaction mixture flowed out would indicate that the content of the Grignard reagent therein become constant and the reaction system reaches a stationary state in 5 to 15 hours usually.

The allyl Grignard reagent thus obtained is useful for the preparation of the phenylalkene derivative of the general formula and hence the 1-bromoalkylbenzene derivative of the general formula (I). It can also be used to be reacted with organic halides, ketones, aldehydes, esters, etc. to prepare intermediates for medicines, agrochemicals, etc.

According to the present invention, 1-bromoalkylbenzene derivatives, phenylalkene derivatives and allyl Grignard reagents can be obtained in high yields, high selectivities and high purities from the starting substances which can be easily available.

EXAMPLES

The present invention will be illustrated by Examples, but is not limited thereto.

Example 1

Into a 3 L four-necked flask equipped with a stirrer, a thermometer, a condenser and a dropping funnel, 37.45 g (1.54 mole) of metal magnesium in a shaved form and 0.1 g of iodine were charged. After the flask was filled with nitrogen, 250 ml of tetrahydrofuran and 750 ml of toluene were added.

The flask was sufficiently cooled on an ice bath, and then 118 g (1.54 mole) of allyl chloride was added dropwise at a temperature of 0° to 20° C. over a period of 2 hours with stirring.

The reaction mixture obtained was flitrated at a room temperature under a nitrogen atmosphere to remove unreacted magnesium. The flitrate was transferred into another 3 L four-necked flask equipped with a stirrer, a thermometer, a condenser and a dropping funnel. Then 130 g (1.03 mole) of benzyl chloride was added dropwise at the same temperature over a period of 30 minutes, followed by stirring the mixture at the same temperature for 4 hours.

After the completion of the reaction, the reaction mixture was added to 300 ml of 5% sulfuric acid at a temperature of 0° to 10° C., followed by stirring for 30 minutes. Thereafter it was allowed to stand and phase-separated. The resulting oil layer was washed with 200 ml of water, followed by phase-separation. The resulting oil layer was transferred to a 3 L four-necked flask equipped with a distilling column. After distilling off the solvent at 110° C. under an atmospheric pressure, the residue was distilled under a reduced pressure of 80 mmHg at 91° C. to obtain 124.3 g of 4-phenyl-1-butene (yield 92%) which was a colorless liquid. An analysis by gas chromatography indicated the purity of 98.8%.

Example 2

Into a 3 L four-necked flask equipped with a stirrer, a thermometer, a condenser and a dropping funnel, 37.45 g (1.54 mole) of metal magnesium in a shaved form and 0.1 g of iodine were charged. After the flask was filled with nitrogen, 500 ml of tetrahydrofuran and 500 ml of tert.-butyl methyl ether were added.

The flask was sufficiently cooled on an ice bath, and then 118 g (1.54 mole) of allyl chloride was added dropwise at a temperature of 0° to 20° C. over a period of 2 hours with stirring.

The reaction mixture obtained was filtrated at a room temperature under a nitrogen atmosphere to remove unreacted magnesium. The flitrate was transferred to another 3 L four-necked flask equipped with a stirrer, a thermometer, a condenser and a dropping funnel. Then 130 g (1.03 mole) of benzyl chloride was added dropwise at the same temperature over a period of 30 minutes, followed by stirring the mixture at the same temperature for 4 hours.

After the completion of the reaction, the reaction mixture was added to 300 ml of 5% sulfuric acid at a temperature of 0° to 10° C., followed by stirring for 30 minutes. Thereafter it was allowed to stand and phase-separated. The resulting oil layer was washed with 200 ml of water, followed by phase-separation. The resulting oil layer was distilled in the similar manner to that in Example 1 to obtain 125.7 g of 4-phenyl-1-butene (yield 93%). An analysis of the product by gas chromatography indicated the purity of 98.0%.

Example 3

Example 1 was repeated except that 1.0 L of tetrahydrofuran was used as a solvent in place of the mixed solvent of 250 ml of tetrahydrofuran and 750 ml of toluene, and 127.0 g (yield 94%) of 4-phenyl-1-butene was obtained. The analysis of the product by gas chromatography indicated the purity of 98.0%.

Example 4

Into a 3 L four-necked flask equipped with a stirrer, a thermometer, a condenser and a dropping funnel, 37.45 g (1.54 mole) of metal magnesium in a shaved form and 0.1 g of iodine were charged. After the flask was filled with nitrogen, 1.0 L of tetrahydrofuran were added.

The flask was sufficiently cooled on an ice bath, and then 118 g (1.54 mole) of allyl chloride was added dropwise at a temperature of 0° to 20° C. over a period of 2 hours with stirring.

The reaction mixture obtained was tiltrated at a room temperature under a nitrogen atmosphere to remove unreacted magnesium. The flitrate was transferred to another 3 L four-necked flask equipped with a stirrer, a thermometer, a condenser and a dropping funnel. 5.58 g (10.3 mmol) of bis(1,3-diphenylphosphinopropane) nickel chloride was added thereto, followed by the dropwise addition of 130 g (1.03 mole) of benzyl chloride at the same temperature over a period of 30 minutes. Then the mixture was stirred at the same temperature for 4 hours.

A posttreatment was effected in the similar manner to that in Example 1 to obtain 132.4 g (yield 96%) of 4-phenyl-1-butene. The analysis of the product by gas chromatography indicated the purity of 98.9%.

Example 5

To 85.5 g of toluene, 2.06 g (15.7 mmol) of 4-phenyl-1-butene prepared in Example 1 was added at a room temperature. The mixture was cooled with ice, followed by stirring for 15 minutes. Then hydrogen bromide gas was blown through the mixture under cooling with ice and the temperature of the mixture was then elevated to a room temperature. After stirring for 1 hour, the reaction mixture was washed with an aqueous sodium bicarbonate solution, and then with water. Then the resulting oil layer was concentrated with a rotary evaporator under a reduced pressure to obtain a colorless liquid. Hydrogen bromide gas was prepared in an amount of 10 mole equivalents (=157 mmol) according to the method known in a literature (see "Inorganic Syntheses", Vol. I, p 149).

The liquid contained 4-phenyl-1-bromobutane and 4-phenyl-2-bromobutane in a ratio of 38:1 by mole.

Example 6

To 40 g of toluene, 4.01 g (30.6 mmol) of 4-phenyl-1-butene prepared in Example 1 was added at a room temperature. The mixture was cooled with ice, followed by stirring for 15 minutes. Then 9.89 g (30.6 mmol) of a solution containing 30% of hydrogen bromide in acetic acid was added dropwise under cooling with ice and the temperature of the mixture was then elevated to the room temperature. After stirring the reaction mixture for 30 minutes, it was washed with an aqueous sodium bicarbonate solution, and then with water. Then the resulting oil layer was concentrated by a rotary evaporator under a reduced pressure to obtain a colorless liquid.

The liquid contained 4-phenyl-1-bromobutane and 4-phenyl-2-bromobutane in a ratio of 20:1 by mole.

Example 7

To 85.5 g of toluene, 2.06 g (15.7 mmol) of 4-phenyl-1-butene prepared in Example 1 was added at a room temperature. The mixture was cooled with ice, followed by stirring for 15 minutes. Then 0.1 g (0.41 mmol) of benzoyl peroxide was added and hydrogen bromide gas prepared in the similar manner to that in Example 1 was blown through the mixture under cooling with ice. The temperature of the mixture was then elevated to a room temperature. After stirring the reaction mixture for 40 minutes, it was washed with an aqueous sodium bicarbonate solution, and then with water. Then the resulting oil layer was concentrated with a rotary evaporator under a reduced pressure to obtain a colorless liquid.

The liquid contained 4-phenyl-1-bromobutane and 4-phenyl-2-bromobutane in a ratio of 41:1 by mole.

Comparative Example 1

3.13 g (115.9 mmol) of a solution containing 30% of hydrogen bromide in acetic acid was cooled with ice and 3.86 g (29.4 mmol) of 4-phenyl-1-butene prepared in Example 1 was added dropwise thereto under cooling with ice. Thereafter the temperature of the mixture was elevated to a room temperature. After stirring the reaction mixture for 15 minutes, it was washed with an aqueous sodium bicarbonate solution, and then with water. Then the resulting oil layer was concentrated with a rotary evaporator under a reduced pressure to obtain a colorless liquid.

The liquid contained 4-phenyl-1-bromobutane and 4-phenyl-2-bromobutane in a ratio of 5:1 by mole.

Example 8

A 200 ml four-necked flask having a branch in such a manner that, when the content therein exceeded 120 ml, the excess amount flowed out of the flask through the branch was equipped with a stirrer, a thermometer, a condenser and a ceptum. 6.56 g (0.27 mol) of metal magnesium in a shaved form, 0.1 g of iodine and 60 ml of a mixed solvent containing 25% by volume of tetrahydrofuran in toluene were charged therein.

The flask was cooled on an ice bath and 156.94 g (2.05 mole) of allyl chloride dissolved in 1200 ml of a mixed solvent containing 25% by volume of tetrahydrofuran in toluene was added dropwise therein at a rate of 60 ml per hour through a pump while maintaining the temperature of the reaction mixture at 25°±2° C. After several minutes, heat was generated with foaming, resulting in a rapid increase of the temperature in the reaction system. Therefore it was cooled with an ice bath to maintain it at 25°±2° C. At the same time with the start of the dropwise addition of allyl chloride, metal magnesium was added at a rate of 2.19 g (0.09 mole) per hour through a continuous rotary solid-introducing apparatus.

The reaction mixture which was flowed out through the branch was sampled every 1 hour, followed by the reaction with n-hexanal. The analysis of the product by gas chromatography indicated that allyl magnesium bromide was obtained in a yield of 82%.

Example 9

Example 8 was repeated except that a mixed solvent containing 50% by volume of tetrahydrofuran in tert.-butyl methyl ether was used in place of the mixed solvent containing 25% by volume of tetrahydrofuran in toluene. Allyl magnesium chloride was obtained in a yield of 80%.

Example 10

Example 8 was repeated except that tetrahydrofuran was used as a solvent in place of the mixed solvent containing 25% by volume of tetrahydrofuran in toluene. Allyl magnesium chloride was obtained in a yield of 82%.

Example 11

Example 8 was repeated except that allyl bromide was used in place of allyl chloride. Allyl magnesium bromide was obtained in a yield of 82%.

Example 12

Example 8 was repeated except that the reaction was carried out at 0° C. in place of 25° C. Allyl magnesium chloride was obtained in a yield of 80%.

Example 13

Example 8 was repeated except that the reaction was carried out at 50° C. in place of 25° C. Allyl magnesium chloride was obtained in a yield of 78%.

Example 14

Example 8 was repeated except that of metal magnesium was initially charged in an amount of 9.84 g (0.41 mole). Allyl magnesium chloride was obtained in a yield of 78%.

Example 15

Example 8 was repeated except that a 300 ml four-necked flask having a branch in such a manner that, when the content therein exceeded 150 ml, the excess amount flowed out of the flask through the branch, was used in place of the 200 ml four-necked flask. Allyl magnesium chloride was obtained in a yield of 83%.

Example 16

Example 8 was repeated except that 4-chloro-2-methyl-2-butene was used in place of allyl chloride. 3-methyl-2-butenyl magnesium chloride was obtained in a yield of 83%.

Example 17

Example 8 was repeated except that 4-chloro-2-butene was used in place of allyl chloride. 2-butenyl magnesium chloride was obtained in a yield of 80%.

Example 18

Example 8 was repeated to form allyl magnesium chloride. The allyl magnesium chloride which flowed out of the flask through the branch was accumulated in a 3 L four-necked flask equipped with a stirrer, a thermometer, a condenser and a dropping funnel which was placed under a nitrogen atmosphere till the completion of the flowing-out of allyl magnesium chloride. Then 156 g (1.23 mole) of benzyl chloride was added dropwise thereto at a temperature of 0° to 20° C. over a period of 45 minutes, followed by stirring at the same temperature for 4 hours.

After the completion of the reaction, a posttreatment was effected in the similar manner to that in Example 1 to obtain 147.7 g (yield 91%, based on benzyl chloride) of 4-phenyl-1-butene which was a colorless liquid. An analysis of the product by gas chromatography indicated the purity of 98.3%.

Example 19

300 g of toluene was added at a room temperature to 15.1 g (0.114 mole) of 4-phenyl-1-butene obtained in Example 18. The mixture was sufficiently cooled by an ice bath and hydrogen bromide prepared in the similar manner to that in Example 5 was blown through it under ice cooling. Then the temperature of the mixture was elevated to a room temperature, followed by stirring for 1 hour. After the mixture was washed with an aqueous sodium bicarbonate solution and then with water, the resulting oil layer was concentrated with a rotary evaporator to obtain a colorless liquid.

The liquid contained 4-phenyl-1-bromobutane and 4-phenyl-2-bromobutane in a ratio of 38:1 by mole.

Example 20

Example 8 was repeated to form allyl magnesium chloride. The allyl magnesium chloride which flowed out of the flask through the branch was accumulated in a 3 L four-necked flask equipped with a stirrer, a thermometer, a condenser and a dropping funnel placed under a nitrogen atmosphere. A mixed solvent of toluene and tetrahydrofuran dissolving allyl chloride was started to be added dropwise thereto. 2 hours after the start of the addition of the mixed solvent, 300 ml of a mixed solvent of toluene and tetrahydrofuran (a content of terahydrofuran 25% by weight) dissolving 156 g (1.23 mole) of benzyl chloride was added dropwise in the 3 L four-necked flask at a rate of 15 ml per hour at a temperature of 0° to 20° C. After the completion of the dropwise addition, the reaction mixture was stirred for 1 hour at the same temperature. After the completion of the reaction, an aftertreatment was effected in a similar manner to that in Example 1 to obtain 146.9 g (yield 90%, based on benzyl chloride) of 4-phenyl-1-butene which was a colorless liquid. An analysis of the product by gas chromatography indicated the purity of 98.7%.

Example 21

300 g of toluene was added at a room temperature to 15.1 g (0.114 mole) of 4-phenyl-1-butene obtained in Example 20. The mixture was sufficiently cooled by an ice bath and hydrogen bromide gas prepared in the similar manner to that in Example 5 was blown through the mixture under ice cooling. Then the temperature of the mixture was elevated to a room temperature, followed by stirring for 1 hour. After the mixture was washed with an aqueous sodium bicarbonate solution and then with water, the resulting oil layer was concentrated with a rotary evaporator under a reduced pressure to obtain a colorless liquid.

The liquid contained 4-phenyl-1-bromobutane and 4-phenyl-2-bromobutane in a ratio of 40:1 by mole.

What is claimed is:

1. A process for preparing bromoalkylbenzene derivative of the formula:

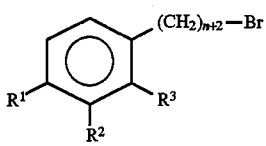  (I)

wherein $R^1$, $R^2$, and $R^3$ independently represent a hydrogen atom, a halogen atom, a lower alkyl group containing 1 to 5 carbon atoms or a lower alkoxy group containing 1 to 5 carbon atoms, or $R^1$ and $R^2$ together form a methylenedioxy group or an ethylenedioxy group when $R^3$ is a hydrogen atom, and n is an integer of 1 to 8, comprising the step of:

reacting a phenylalkene derivative of the formula:

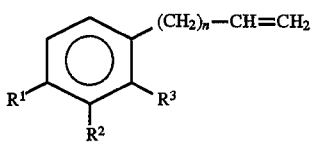  (II)

wherein $R^1$, $R^2$, $R^3$ and n are the same as defined above with hydrogen bromide in the presence of a non-polar solvent to form the 1-bromoalkylbenzene derivative of the formula (I).

2. The process of claim 1, wherein the reaction is carried out in the presence of a radical initiator.

3. The process of claim 2, wherein said radical initiator is a peroxide.

4. The process of claim 2, wherein said radical initiator is AIBN.

5. The process of claim 2, wherein said radical initiator is light.

6. The process of claim 2, wherein said radical initiator is oxygen.

7. A process for preparing a 1-bromoalkylbenzene derivative of the formula (I)

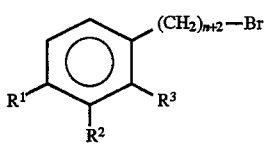  (I)

wherein $R^1$, $R^2$, and $R^3$ independently represent a hydrogen atom, a halogen atom, a lower alkyl group containing 1 to 5 carbon atoms or a lower alkoxy group containing 1 to 5 carbon atoms, or $R^1$ and $R^2$ together form a methylenedioxy group or an ethylenedioxy group when $R^3$ is a hydrogen atom, and n is an integer of 1 to 8, comprising the steps of:

reacting an alkenyl halide of the formula (III)

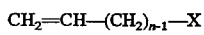

$$CH_2=CH-(CH_2)_{n-1}-X \quad (III)$$

wherein X represents a chlorine atom or a bromine atom and n is an integer of 1 to 8 with metal magnesium to form a Grignard reagent of the formula (IV)

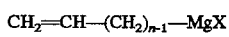

$$CH_2=CH-(CH_2)_{n-1}-MgX \quad (IV)$$

wherein X and n are the same as defined above;

reacting the Grignard reagent of the formula (IV) with a benzyl halide derivative of the formula (V)

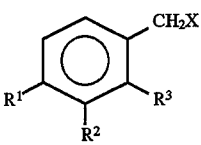  (V)

wherein $R^1$, $R^2$, $R^3$ and X are the same as defined above to form a phenylalkene derivative of the formula (II)

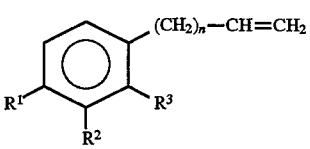  (II)

wherein $R^1$, $R^2$, $R^3$ and n are the same as defined above; and reacting the phenylalkene derivative of the formula (II) with hydrogen bromide in the presence of a non-polar solvent to form the 1-bromoalkylbenzene derivative of the formula (I).

8. A process for preparing a 1-bromoalkylbenzene of the formula (I)

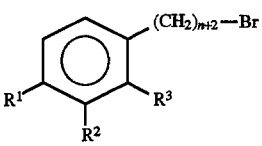  (I)

wherein $R^1$, $R^2$, and $R^3$ independently represent a hydrogen atom, s halogen atom, a lower alkyl group containing 1 to 5 carbon atoms or a lower alkoxy group containing 1 to 5 carbon atoms, or $R^1$ and $R^2$ together form a methylenedioxy group or an ethylenedioxy group when $R^3$ is a hydrogen atom, and n is 2, comprising the steps of:

reacting continuously an allyl halide derivative of the formula (VII)

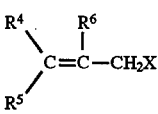  (VII)

wherein $R^4$, $R^5$ and $R^6$ are all hydrogen atoms with metal magnesium in an organic solvent to form an allyl Grignard reagent of the formula (VI)

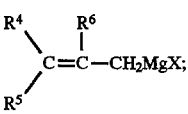  (VI)

reacting the allyl Grignard reagent (VI) with a benzyl halide derivative of the formula (V)

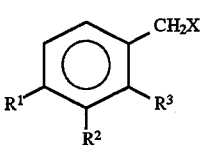  (V)

wherein $R^1$, $R^2$, $R^3$ and X are as defined above in an organic solvent to form the phenylalkene derivative of the formula (II)

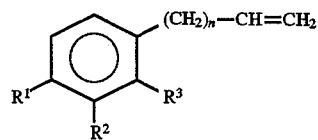 (II)
wherein $R^1$, $R^2$, $R^3$ and n are as defined above; and
reacting the phenylalkene derivative of the formula (II) with hydrogen bromide to form the 1-bromoalkylbenzene of the formula (I).
* * * * *